United States Patent [19]

Partyka et al.

[11] Patent Number: 4,458,079

[45] Date of Patent: Jul. 3, 1984

[54] SULFUR-CONTAINING IMIDAZOLES

[75] Inventors: Richard A. Partyka, Liverpool; Thomas W. Hudyma, Manlius, both of N.Y.

[73] Assignee: Bristol-Myers Company, New York, N.Y.

[21] Appl. No.: 176,422

[22] Filed: Aug. 8, 1980

[51] Int. Cl.$^3$ .......................................... C07D 233/60
[52] U.S. Cl. .................................. 548/341; 424/263; 424/273 R; 546/256; 546/278; 548/336
[58] Field of Search ............... 546/256, 278; 548/336, 548/341; 424/263, 273 R

[56] References Cited

U.S. PATENT DOCUMENTS

| | | | |
|---|---|---|---|
| 3,531,494 | 9/1970 | Adolphi et al. | 548/341 X |
| 3,717,655 | 2/1973 | Godefroi et al. | 548/341 |
| 3,793,453 | 2/1974 | Godefroi et al. | 424/273 R |
| 3,796,704 | 3/1974 | Metzger et al. | 548/341 X |
| 3,936,470 | 2/1976 | Heeres | 548/336 |
| 4,036,970 | 7/1977 | Walker et al. | 548/341 X |
| 4,036,973 | 7/1977 | Walker et al. | 548/341 X |
| 4,055,652 | 10/1977 | Walker | 424/273 R |
| 4,062,966 | 12/1977 | Gymer | 548/336 X |
| 4,107,314 | 8/1978 | Cox et al. | 546/278 X |

FOREIGN PATENT DOCUMENTS 1654 5/1979 European Pat. Off. .

OTHER PUBLICATIONS

Blicke, F., in *Thiophene and Its Derivatives*, by H. D. Hartough, Interscience, New York, 1952, p. 29.
Conant, J., *The Chemistry of Organic Compounds*, MacMillan Co., New York, 1947, p. 264.
Noller, C., *Chemistry of Organic Compounds*, 2nd Ed., W. B. Saunders, Philadelphia, 1957, p. 382.
Royals, E., *Advanced Organic Chemistry*, Prentice-Hall, New York, 1954, p. 637.

Primary Examiner—Richard A. Schwartz
Attorney, Agent, or Firm—Richard R. Lloyd

[57] ABSTRACT

Novel imidazole mercaptals of the formula

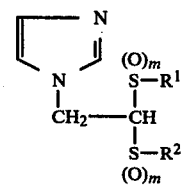

wherein each m is independently zero or one; and $R^1$ and $R^2$ each are independently selected from (lower)alkyl, cycloalkyl, cycloalkyl(lower)alkyl, phenyl, phenyl(lower)alkyl, thienyl, thienyl(lower)alkyl, pyridyl and pyridyl(lower)alkyl, in which the phenyl and heterocyclic rings optionally may contain from 1 to 3 substituents, and acid addition salts thereof, are useful antimicrobial agents.

9 Claims, No Drawings

SULFUR-CONTAINING IMIDAZOLES

SUMMARY OF THE INVENTION

This invention relates to antimicrobial agents, i.e. to compounds having both antifungal and antibacterial activity. More particularly, this invention relates to antimicrobial imidazole mercaptals of the general formula

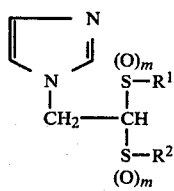

wherein each m is independently zero or one; and $R^1$ and $R^2$ each are independently selected from (lower)alkyl, cycloalkyl, cycloalkyl(lower)alkyl, phenyl, phenyl(lower)alkyl, thienyl, thienyl(lower)alkyl, pyridyl and pyridyl(lower)alkyl, in which the phenyl and heterocyclic rings optionally may contain from 1 to 3 substituents; and acid addition salts thereof. This invention also relates to a process for the preparation of said antimicrobial agents, to compositions containing said antimicrobial agents and to methods of using said antimicrobial agents or compositions containing the same.

BACKGROUND AND PRIOR ART

A large number of 1-(β-aryl)ethyl-1H-imidazole antifungal and antibacterial agents are known, but the imidazole mercaptals of Formula I have not previously been reported in the literature.

U.S. Pat. No. 3,717,655 discloses 1-(β-aryl)ethylimidazole ethers and amines of the formula

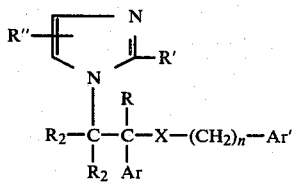

in which R, $R_1$ and $R_2$ each are selected from hydrogen and (lower)alkyl; X is oxygen or NH; n is 1 or 2; Ar is phenyl [optionally substituted by halogen, (lower)alkyl or (lower)alkoxy], thienyl or halothienyl; Ar' is phenyl [optionally substituted by halogen (lower)alkyl, (lower)alkoxy; cyano, nitro or amino] or α-tetralyl; R' is hydrogen, methyl or ethyl; and R" is hydrogen or methyl; provided that (i) when X is NH, R is hydrogen; (ii) when Ar' is nitrophenyl or aminophenyl, X is oxygen and n is zero; (iii) when Ar' is α-tetralyl, X is NH and n is zero; and (iv) when X is oxygen and Ar' is phenyl, halophenyl, (lower)alkylphenyl, (lower)alkoxyphenyl or cyanophenyl, then n is other than zero; and therapeutically active acid addition salts thereof. The compounds are stated to have antifungal and antibacterial activity.

U.S. Pat. No. 4,055,652 discloses substituted 1-phenethylimidazoles of the formula

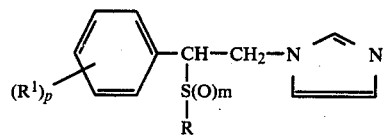

wherein R is alkyl, alkenyl, aralkenyl, substituted aralkenyl, alkynyl, cycloalkyl, cycloalkyl alkyl, aralkyl, substituted aralkyl, aryl or substituted aryl, in which the substituents are selected from one or more of halogen, lower alkyl, lower alkoxy, trifluoromethyl, nitro and cyano, provided that the substituents on the substituted aryl may also be amino or acylamino; $R^1$ is hydrogen, halogen, lower alkyl, lower alkoxy, trifluoromethyl, nitro, cyano, thiocyano or the group

in which $R^2$ is alkyl, cycloalkyl, aralkyl substituted aralkyl, aryl or substituted aryl, in which the substituents are selected from one or more halogen, lower alkyl, lower alkoxy, trifluoromethyl, nitro and cyano moieties; and m, n and p each are independently 0, 1 or 2, provided that m cannot be greater than n except when $R^1$ is the group

and $R^2$ is aryl or substituted aryl; and the antimicrobial acid addition salts thereof. The compounds are stated to be useful antifungal, antibacterial and antiprotozoal agents.

U.S. Pat. No. 4,036,970 discloses β,γ-disubstituted propylimidazoles of the formula

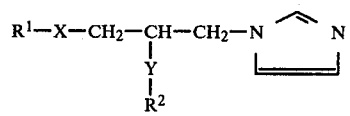

wherein $R^1$ and $R^2$ each are phenyl or benzyl which optionally contain on the phenyl rings one or more substituents selected from halogen, (lower)alkyl and trifluoromethyl; X and Y each are independently oxygen or sulfur, with the proviso that Y is not oxygen when $R^2$ is phenyl or substituted phenyl; and the antimicrobial acid addition salts thereof. The compounds are stated to be useful as antifungal, antibacterial and antiprotozoal agents. The disclosure of U.S. Pat. No. 4,036,973 is substantially the same except that one of $R^1$ and $R^2$ must be alkyl or cyclohexylalkyl.

U.S. Pat. No. 3,796,704 discloses phenylimidazolylalkanyl derivatives of the formula

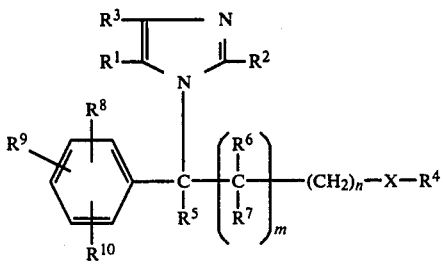

in which R¹, R² and R³ each are selected from hydrogen and (lower)alkyl; R⁴ is hydrogen or an optionally substituted alkyl, alkenyl, alkynyl, aryl, aralkyl, aralkenyl, aralkynyl, aliphatic acyl, aromatic acyl or —R⁴'—O—R⁴"— group, where R⁴' and R⁴" are saturated or unsaturated hydrocarbon groups, alkylsulfonyl, alkenylsulfonyl, alkynylsulfonyl, arylsulfonyl or a group of the formula

in which Y is oxygen or sulfur, and R¹² is an optionally substituted lower alkoxy, lower alkenyloxy, lower alkynyloxy, lower alkylmercapto, lower alkenylmercapto, lower alkynylmercapto, aryloxy, arylmercapto, amino, mono(lower alkyl-, lower alkenyl-, or lower alkynyl-)amino, monoarylamino, diarylamino, arylsulfonamido or —N(lower alkyl)—CO—NH—lower alkyl group; R⁵ is hydrogen or an alkyl, alkenyl, alkynyl or optionally substituted aryl radical; R⁶ and R⁷ each are selected from hydrogen or an optionally substituted alkyl, alkenyl, alkynyl or aryl radical; R⁸, R⁹ and R¹⁰ each are selected from hydrogen or a lower alkyl, lower alkenyl, lower alkynyl, lower alkoxy or lower alkylthio group, or an electronegative group; X is oxygen, sulfur, —SO—, —SO₂—, —NH— or an

group, in which R" is hydrogen, lower alkyl, lower alkenyl or lower alkynyl; m is an integer of 1-6; and n is 0 or 1; and salts thereof. The compounds are stated to have antimycotic activity.

Published European patent application No. 1654 discloses substituted 1-phenethylimidazoles of the formula

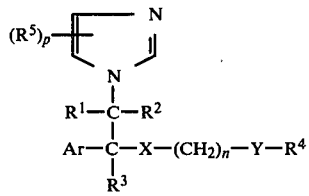

wherein R¹, R² and R³ are independently hydrogen or lower alkyl; R⁴ is hydrogen, lower alkyl or a cycloalkyl, benzyl or phenyl group which may contain one or more halogen, lower alkyl, lower alkoxy, lower alkylthio, phenyl, cyano, nitro or amino substituents, or a pyridyl group which is optionally substituted by halogen; R⁵ is nitro or lower alkyl; Ar is a phenyl group optionally substituted by one or more halogen, lower alkyl, lower alkoxy or cycloalkyl moieties, or a benzyl group optionally substituted by a substituent named under R⁴; X and Y are independently oxygen or sulfur; n is an integer of from 1 to 5; and p is 0, 1, 2 or 3; and pharmacologically acceptable acid addition salts thereof. The compounds are stated to be antimycotic and antibacterial agents.

U.S. Pat. No. 3,793,453 discloses 1-(β-aryl)ethylimidazole ketals of the formula

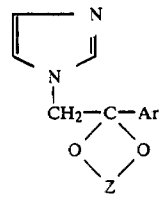

in which Z is —CH₂CH₂—, —CH₂CH₂CH₂—, —CH₂CH(CH₃)— or —CH(CH₃)CH(CH₃)—; and Ar is phenyl, halophenyl, dihalophenyl, trihalophenyl, (lower)alkylphenyl, (lower)alkoxyphenyl, nitrophenyl or 2-thienyl; and the therapeutically active acid addition salts thereof. The compounds are stated to have antibacterial and antifungal activity. U.S. Pat. No. 3,936,470 has a similar disclosure except that Ar may not be nitrophenyl or 2-thienyl; and Z is the group

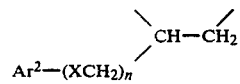

in which Ar² is phenyl, naphthyl, halonaphthyl or phenyl having from 1 to 3 substituents selected from halo, loweralkyl, loweralkoxy, cyano, phenyl and benzyl; X is oxygen, sulfur or methylene; and n is 0 or 1.

COMPLETE DISCLOSURE

This invention relates to novel antimicrobial agents having the general formula

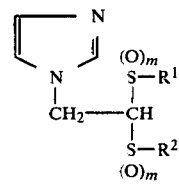

wherein R¹ and R² each are independently selected from (lower)alkyl, cycloalkyl of from 4 to 7 carbon atoms, cycloalkyl(lower)alkyl having from 3 to 7 carbon atoms in the cycloalkyl ring, phenyl, phenyl(lower)alkyl, thienyl, thienyl(lower)alkyl, pyridyl and pyridyl(lower)alkyl, provided that the phenyl, thienyl and pyridyl rings may contain from 1 to 3 substituents independently selected from chloro, bromo, fluoro, trifluoromethyl, trifluoromethylthio, (lower)alkyl, (lower)alkenyl, (lower)alkynyl, (lower)alkoxy, (lower)alkylthio, nitro, amino, (lower)alkylamino, di(lower)alkylamino, (lower)alkanoylamino, cyano, carboxy and carbo(lower)alkoxy; and each m is independently selected from 0 and 1; and acid addition salts thereof.

The compounds of Formula I exhibit antifungal and antibacterial activity against animal and human pathogens, as well as antifungal activity against fungi which are primarily of agricultural or industrial importance.

In another aspect, this invention relates to methods of inhibiting the growth of fungi and bacteria by administering to a human or animal host, or host object, containing, or subject to attack by, fungi or bacteria, a fungicidally or bactericidally effective amount of a compound of Formula I. In still another aspect, this invention relates to compositions suitable for pharmaceutical, agricultural and industrial use, which compositions comprise at least one compound of Formula I in combination with a suitable carrier.

As used herein and in the claims, the term "(lower)alkyl," "(lower)alkoxy" or "(lower)alkylthio" means an alkyl, alkoxy or alkylthio group, either straight or branched, containing from 1 to about 8 carbon atoms; preferred groups contain from 1 to 6 carbon atoms. The term "(lower)alkanoyl," "(lower)alkenyl" or "(lower)alkynyl" means an alkanoyl, alkenyl or alkynyl group, either straight or branched, containing from 2 to about 8 carbon atoms; preferred groups contain from 2 to 6 carbon atoms.

The compounds of Formula I are organic bases, the majority of which are viscous oils in the free base form. If desired, the free bases may be converted to a solid acid addition salts by contacting them with an appropriate inorganic or organic acid, usually in a solvent such as water, ethanol, 1-propanol, ethyl acetate, acetonitrile or diethyl ether, or a mixture thereof. Upon removal of the solvent, cooling or dilution with a less polar solvent, the crystalline acid addition salts are obtained.

It will be appreciated that, when used in agricultural or industrial applications, the acid addition salts of the compounds of Formula I need not be "pharmaceutically acceptable," but may be a salt formed with essentially any acid. Acids which are useful for preparing "pharmaceutically acceptable" acid addition salts of the compounds of Formula I are well-known to those skilled in the art, and include inorganic acids such as hydrochloric, hydrobromic, hydroiodic, nitric, sulfuric and phosphoric acids, and organic acids such as fumaric, oxalic, maleic, acetic, pyruvic, citric, tartaric, methanesulfonic, ethanesulfonic, p-toluenesulfonic, hydroxyethanesulfonic, sulfamic, malic, succinic, ascorbic, levulinic, propionic acids and the like.

When $R^1$ and $R^2$ are different, and β-carbon of the N-ethyl group is asymmetric and the compound of Formula I therefore will exist in two optically active enantiomeric forms as well as the racemic mixture. If desired, the racemic mixture may be separated into the two enantiomers by the conventional procedure of resolution through the use of an optically active acid such as camphor-10-sulfonic acid, camphoric acid, methoxyacetic acid, tartaric acid, malic acid, diacetyltartaric, pyrrolidone-5-carboxylic acid, or the like. Various other combinations of stereoisomers are also possible. Thus, whether $R^1$ and $R^2$ are the same or different, if one of the sulfur atoms is oxidized to a sulfinyl moiety, the resulting compound will have two asymmetric centers and will exist as two diastereoisomeric forms. The diastereoisomers may be separated by conventional means such as fractional crystallization. Further, when each m is zero, and $R^1$ and $R^2$ are the same but themselves contain an asymmetric center, the compound of Formula I will exist as one d,l-pair (racemic form which can be resolved into its two enantiomers) and two meso forms. It is to be understood that this invention includes all stereoisomeric forms of the compounds of Formula I, as individual separated entities as well as mixtures thereof.

The compounds of Formula I contain the mercaptal grouping

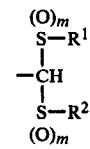

on the carbon atom which is α to the imidazole ring. It is this α-mercaptal grouping which readily distinguishes the compounds of this invention from the prior art antifungal agents. The compounds of Formula I are named as derivatives of 1-ethyl-1H-imidazole, with the substituents

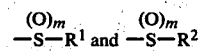

located on the 2-position (or β-position) of the ethyl side chain.

Preferred compounds of the present invention are those of Formula I in which $R^1$ and $R^2$ are the same or different and are phenyl, phenyl(lower)alkyl or thienyl(lower)alkyl, in which the phenyl and thienyl rings optionally contain one or more substituents independently selected from chloro, bromo, fluoro, trifluoromethyl, (lower)alkyl, (lower)alkenyl, (lower)alkynyl, (lower)alkoxy, (lower)alkylthio, nitro, amino, (lower)alkylamino, di(lower)alkylamino, cyano, carboxy and carbo(lower)alkoxy.

In a more preferred embodiment of the compounds of Formula I, $R^1$ and $R^2$ are the same or different and are phenyl, benzyl, phenethyl or thienylmethyl, in which the phenyl and thienyl rings optionally contain one or more substituents independently selected from chloro, fluoro, trifluoromethyl, (lower)alkyl, (lower)alkoxy, (lower)alkylthio, nitro, amino, cyano, carboxy and carbo(lower)alkoxy.

In a still more preferred embodiment of the compounds of Formula I, $R^1$ and $R^2$ are the same or different and are phenyl, benzyl, phenethyl or thienylmethyl, in which the phenyl and thienyl rings optionally contain 1 or 2 substituents independently selected from chloro, fluoro, trifluoromethyl, methyl, methoxy, methylthio, nitro, amino, cyano, carboxy and carbomethoxy.

As presently envisaged, particularly preferred compounds of Formula I are
1-[2,2-bis(4-methylbenzylthio)ethyl]-1H-imidazole,
1-[2,2-bis(4-chlorobenzylthio)ethyl]-1H-imidazole,
1-[2,2-bis(2,4-dichlorobenzylthio)ethyl]-1H-imidazole,
1-[2-(4-chlorophenylthio)-2-(2,6-dichlorobenzylthio)ethyl]-1H-imidazole,
1-[2,2-bis(2,6-dichlorobenzylthio)ethyl]-1H-imidazole,
1-[2,2-bis(4-methylthiobenzylthio)ethyl]-1H-imidazole,
1-[2,2-bis(5-chloro-2-thienylmethylthio)ethyl]-1H-imidazole,
1-[2,2-bis(2-chloro-3-thienylmethylthio)ethyl]-1H-imidazole,
1-[2-(4-chlorobenzylthio)-2-(4-chlorophenylthio)ethyl]-1H-imidazole and
1-[2-(4-chlorophenylthio)-2-(4-methylbenzylthio)ethyl]-1H-imidazole, and acid addition salts thereof.

The compounds of Formula I in which $R^1$ and $R^2$ are the same are prepared by reacting 2-(imidazol-1-yl)acetaldehyde (II) or an acetal thereof having the Formula III

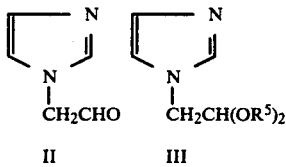

wherein $R^5$ is (lower)alkyl or a phenyl or phenyl(lower-)alkyl group which may contain from 1 to 3 substituents in the phenyl ring, with about two moles (per mole of Compound II or III) of a mercaptan $R^1SH$ (IVa), wherein $R^1$ is as defined above, in the presence of at least one Lewis acid, and optionally in the presence of an inert organic diluent.

Suitable Lewis acids are well known to those skilled in the art and include, for example, boron trifluoride etherate, aluminum chloride, zinc chloride, methanesulfonic acid, benzenesulfonic acid, toluenesulfonic acid, naphthalenesulfonic acid, sulfuric acid, phosphoric acid, hydrogen chloride, acetic acid, propionic acid, and the like. If the Lewis acid is a liquid such as acetic acid, it may be used in excess and serve as a solvent for the reaction. When the Lewis acid is a solid such as toluenesulfonic acid, one may also utilize acetic acid as a solvent, or may utilize an inert organic diluent such as chloroform, methylene chloride, carbon tetrachloride, benzene, toluene, xylene, dimethylacetamide, dimethylformamide, diethyl ether, diglyme, or the like. We usually prefer to use boron trifluoride etherate as the Lewis acid and acetic acid or a mixture of acetic acid and an inert diluent (preferably chloroform, methylene chloride or toluene) as solvent.

It is usually preferred to use the imidazolyl starting material in the form of its acetal (III) rather than as the aldehyde (II) since the former is readily prepared from sources other than the aldehyde. In acetal III, $R^5$ is preferably (lower)alkyl and most preferably methyl or ethyl.

The reaction may be conducted over a temperature range of from about 0° to about 165°. The reaction often tends to be slow at the lower temperatures while, at the higher temperatures, side reactions leading to lower yields or lower purity often occur. We therefore prefer to conduct the reaction within the temperature range of from about 0° to about 125°, and most preferably from about room temperature to about 125°. It is most convenient to maintain the desired temperature by utilizing the appropriate solvent or diluent and conducting the reaction at reflux temperature.

The reaction mixture is readily worked up by concentrating to dryness and treating the residue with an aqueous base such as sodium hydroxide or potassium hydroxide, to yield the product in its free base form. The free base may then, if desired, be converted to an acid addition salt, as described above.

The overall reaction scheme is illustrated below for the preparation of one of the preferred compounds of the invention, utilizing boron trifluoride etherate, chloroform and acetic acid, and starting with the acetal in which $R^5$ is ethyl.

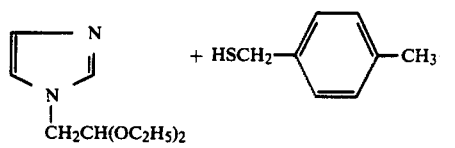

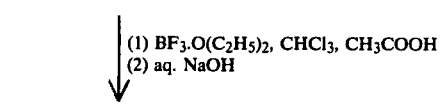

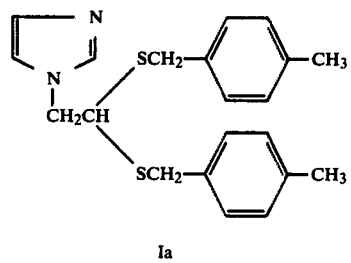

When preparing compounds of Formula I in which $R^1$ and $R^2$ are different (unsymmetrical products), the reaction scheme is the same as described above except that, instead of using about 2 moles of mercaptan IVa (per mole of starting compound II or III), one utilizes about one mole each of mercaptans $R^1SH$ (IVa) and $R^2SH$ (IVb), in which $R^1$ and $R^2$ are the desired substituent groups. Workup of this reaction mixture gives a mixture of the three possible products (Ib-d), with the unsymmetrical product Ib predominating.

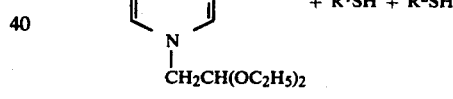

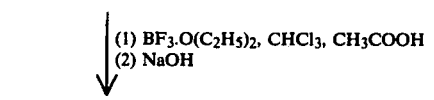

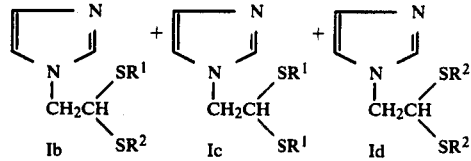

The desired unsymmetrical product Ib is then separated from the symmetrical products by any of the methods commonly employed in the art, such as distillation, fractional crystallization of their solid acid addition salts, gas-liquid chromatography, high pressure liquid chromatography, ion exchange chromatography or the various column chromatography techniques utilizing material such as silica gel or the like. We usually find it most convenient to convert the mixture of free bases to solid acid addition salts and to separate the desired unsymmetrical product by fractional crystallization.

If it is desired to obtain a product of Formula I in the sulfoxide form, i.e. wherein either (or each) m is one, the corresponding product of Formula I wherein each m is zero may be oxidized in a conventional manner to produce the desired product in the sulfoxide form. We normally prefer to utilize m-chloroperbenzoic acid for this oxidation, in an inert solvent such as chloroform. The oxidation is readily accomplished at room temperature.

When preparing compounds of Formula I in which $R^1$ and/or $R^2$ contain certain substituents such as amino, it sometimes may be preferable to protect the amino group in the starting material with a conventional amino-blocking group, and then remove the amino-blocking group from the product by conventional means. Alternatively one may, if desired, utilize a starting material in which $R^5$ contains a corresponding nitro group and subsequently reduce the nitro group of the product to an amino group by conventional means, e.g. with iron powder in aqueous $NH_4Cl$.

The antifungal activity of some of the compounds of Formula I against a number of human and animal pathogenic fungi is given in Table I for either a liquid medium (Sabouraud broth) or an agar medium (Sabouraud broth plus 1% ionagar). Two-fold serial dilutions were made with Sabouraud's liquid medium from stock solutions of the test compounds, usually in dimethyl sulfoxide, N,N-dimethylformamide or water. The Minimum Inhibitory Concentrations (MIC's), which were considered to be the minimum concentrations of the test compounds in micrograms per milliliter which prevent grossly detectable growth of the test organisms, were then determined after inoculation of the medicated broths with the test organisms, and incubation at the appropriate temperature and for the appropriate time interval. Candida species were incubated for 24 hours at 37°, while the dermatophytes *Trichophyton rubrum*, *Trichophyton mentagrophytes* and *Microsporum canis* were incubated for five days at 28°. The agar dilution assay was essentially the same as the broth dilution assay except that 1% inoagar was added to the Sabouraud broth.

Some of the compounds of Formula I have been tested against a Candida vaginal infection in mice and and a Trichophyton skin infection in guinea pigs and have shown good in vivo activity.

Starting materials of Formula III may themselves be prepared from imidazole by forming the sodium salt thereof (such as with sodium hydride in an inert solvent such as dimethylformamide) and then reacting the sodium salt with the appropriate 2-haloacetaldehyde acetal (V), as illustrated by the following reaction scheme

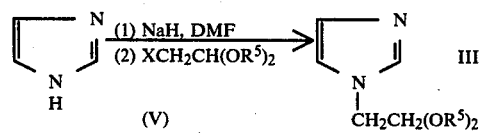

in which $R^5$ is as described above and X is chloro or bromo. The sodium salt of imidazole also can be generated by the use of sodium methoxide instead of sodium hydride. In that procedure the methanol which is formed is preferably distilled from the reaction vessel prior to the introduction of Compound V. The preparation of Compound III in which $R^5$ is ethyl is described in French Pat. No. 1,486,817 and is shown in Illustrative Procedure No. 1, below. Analogous and homologous compounds are prepared by the same procedure, but using the appropriately substituted acetal of Formula V.

A majority of the mercaptans of Formula IV utilized in preparing the compounds of the present invention are described in the prior art and many are commercially available. Those which are not previously described can be prepared by well-established techniques. For example, 2-chloro-3-thienylmethylmercaptan (VI) and 2-(4-chlorophenyl)ethanethiol (VII) were synthesized by the general method of Frank and Smith, J. Amer. Chem. Soc., 68, 2103 (1946), and their preparation is given below in Illustrative Procedures No. 2 and 3, respectively.

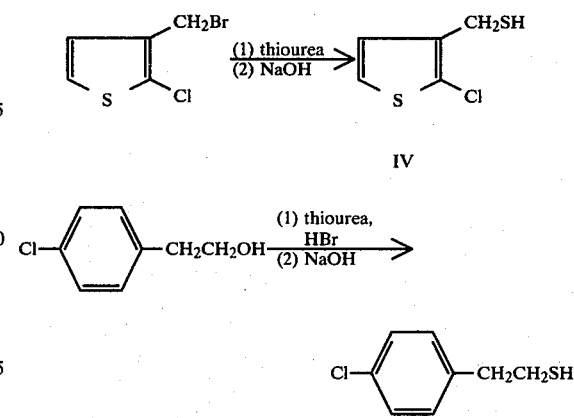

TABLE I

Susceptibility of Various Yeasts and Dermatophytes to Imidazole Mercaptal Derivatives

| Compound of Example No. | Candida albicans A 9540 | Candida A 15049 | Candida tropicalis A 1505 | Candida krusei A 15051 | A 15052 | Trichophyton rubrum A 22789 | Trichophyton mentagrophytes A 9870 | Microsporum canis A 9872 | A 22494 |
|---|---|---|---|---|---|---|---|---|---|
| | | | | MIC (μg/ml) in Sabouraud Broth | | | | | |
| 1 | 1 | 2 | 2 | >16 | 0.5 | 0.063 | 0.032 | 0.032 | 0.063 |
| 2(g) | >16 | >16 | >16 | >16 | >16 | 0.063 | 0.063 | 0.032 | 0.063 |
| 2(j) | 4 | 4 | 4 | >16 | 8 | 0.063 | 0.063 | 0.063 | 0.063 |
| 2(l) | >16 | >16 | >16 | >16 | 8 | 0.063 | 0.063 | 0.063 | 0.13 |
| | | | | MIC (μg/ml) in Sabouraud Broth Plus 1% Ionagar | | | | | |
| 2(h) | 8 | 16 | 16 | 63 | 32 | 0.5 | 1 | 1 | 0.25 |
| 2(p) | 4 | 4 | 4 | 125 | 8 | 0.5 | 0.5 | 0.25 | 0.032 |
| 5 | 4 | 4 | 4 | 32 | 4 | 0.25 | 0.063 | 0.25 | 0.032 |

Many thiophenols and heterocyclic mercaptans such as 2-, 3- and 4-pyridylmercaptan, and their substituted analogs, can be prepared by the general procedure of Newman and Karnes, J. Org. Chem., 31, 3980 (1966). Numerous aromatic and heterocyclic systems can be chloromethylated by the use of formaldehyde and hydrogen chloride. The resulting chloromethyl compounds readily can be converted to the corresponding thiols by established techniques.

The antimicrobial compounds of this invention exhibit antifungal and antibacterial activity against a wide variety of human and animal pathogens in addition to those referred to in Table I above and are accordingly useful not only in pharmaceutical applications but also in agricultural, industrial, household and other applications in which such activity is required. In general, antimicrobial compositions may contain such compounds in any concentrations, i.e. from about 0.1% to about 99.9% in a suitable or conventional carrier adapted for the intended use. For example, from about 10% to 90% concentrates may be supplied for dilution by the user to concentrations generally ranging from about 0.1% to 10%.

In pharmaceutical formulations compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline, petrolatum and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials.

The pharmaceutical compositions of this invention typically comprise a pharmaceutically acceptable, non-toxic carrier in combination with one or more compounds of Formula I in an amount effective for relief or prevention of the specific condition being treated. Since the active compounds of this invention exhibit anti-fungal and anti-bacterial activity over a wide range of concentration, the effective amount may vary. For example, in topical formulations the amount may be about 0.1% to about 10% of the total pharmaceutical formulation while in other formulations the amount may be about 5 to 95% or more. Preferably the pharmaceutical compositions of this invention are formulated in unit dosage form to facilitate administration (unit dosage being the amount of active ingredients administered on one occasion).

In pharmaceutical applications, the subject compounds and compositions may be administered to humans and animals by conventional methods, e.g. topically, orally, parenterally and the like. "Topical" administration includes intravaginal application while parenteral administration includes intramuscular as well as subcutaneous and intravenous injection. Intravenous injection of imidazole derivatives for certain systemic conditions has been demonstrated to be effective (see, for example, Drugs 9, 419–420 (1975), which describes the intravenous administration of Miconazole, i.e. 1-[2,4-dichloro-$\beta$-(2',4'-dichlorobenzyloxy)phenethyl]-imidazole nitrate, to patients with systemic candidiasis). Topical application is the preferred method of administration in pharmaceutical applications. For such treatment, an area having an existing fungal or bacterial growth, or to be protected against attack by fungi or bacteria, may be treated with the subject compounds of Formula I or compositions containing them by, for example, dusting, sprinkling, spraying, rinsing, brushing, dipping, smearing, coating, impregnating and the like.

The exact regimen for pharmaceutical administration of the compounds and compositions disclosed herein will necessarily be dependent upon the needs of the individual subject being treated, the type of treatment, e.g. whether preventative or curative, the type of organism involved and, of course, the judgment of the attending practitioner. In general, for systemic (e.g., oral or parenteral) administration it is expedient to administer the active ingredient in amounts of between about 1 and 100 mg/kg body weight per day (preferably between about 5 and 50 mg/kg body weight per day) preferably distributed over several applications (e.g., in 3 individual doses) in order to achieve effective results. For localized (e.g., topical) administration, however, proportionately less of the active ingredient is required.

In agricultural applications, the subject compounds may be applied directly to plants (e.g., seeds, foliage) or to soil. For example, the compounds of the present invention may be applied to seeds alone or in admixture with a powdered solid carrier. Typical powdered carriers are the various mineral silicates, e.g., mica, talc, pyrophyllite and clays. The subject compounds may also be applied to the seeds in admixture with a conventional surface-active wetting agent with or without additional solid carrier. Surface-active wetting agents that can be used are any of the conventional anionic, non-ionic, amphoteric or cationic types. As a soil treatment for fungi and the like, the subject compounds can be applied as a dust in admixture with sand, soil or a powdered solid carrier such as mineral silicate with or without additional surface-active agent, or the subject compounds can be applied as an aqueous spray optionally containing a surface-active dispersing agent and a powdered solid carrier. As a foliage treatment, the subject compounds can be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase the effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

This invention has been disclosed with respect to certain preferred embodiments, and it will be understood that modifications and variations thereof obvious to those skilled in the art are to be included within the spirit and perview of this application and the scope of the appended claims.

In the following Illustrative Procedures and Examples, all temperatures are given in degrees Centigrade.

ILLUSTRATIVE PROCEDURE NO. 1

Preparation of 1-(2,2-diethoxyethyl)-1H-imidazole

A solution of imidazole (68.08 g, 1.0 mole) in DMF (200 ml) was added dropwise over a period of 20 minutes to a stirred, cooled (ice-H$_2$O) mineral oil suspension of 57% sodium hydride (44.2 g, 1.05 mole) in DMF (100 ml). When the vigorous evolution of hydrogen subsided, the mixture was stirred on a water bath at 50° for 20 minutes to complete salt formation. The mixture was again cooled in an ice-H$_2$O bath and a solution of 1-bromo-2,2-diethoxyethane (197.1 g, 1.0 mole) in DMF (50 ml) was added dropwise over a period of 20 minutes. The mixture was then heated on a steam bath until an exothermic reaction started. The temperature was maintained at 120° by external cooling. When the exothermic reaction subsided, stirring was continued at 135°–140° for 75 minutes. The mixture was cooled and filtered to remove the sodium bromide. The DMF was removed on a rotary evaporator and the residue distilled to provide the titled acetal, 153.8 g (83% yield), bp 90°–95° (0.1 mm).

ILLUSTRATIVE PROCEDURE No. 2

Preparation of 2-chloro-3-thienylmethyl mercaptan

A solution of 2-chloro-3-thienylmethyl bromide (5.36 g, 0.0254 mole) and thiourea (1.94 g, 0.0254 mole) in 95% ethanol (12 ml) was heated under reflux for 4 hours and concentrated to leave the crystalline isothiouronium salt. The salt was suspended in water (20 ml) containing sodium hydroxide (1.52 g, 0.038 mole) and the mixture warmed for 2 hours on a steam bath. The cooled mixture was acidified with 6N HCl (7 ml) and extracted with diethyl ether. The ethereal extract was washed with water and dried (Na$_2$SO$_4$). Removal of the ether left 3.7 g of the title compound, a portion of which was distilled in a Kugelrohr apparatus to provide the analytical sample, bp 126°–128° (15 mm) as a colorless oil.

Anal. Calcd. for C$_5$H$_5$ClS$_2$: C, 36.46; H, 3.06; Cl, 21.53; S, 38.94. Found: C, 35.95; H, 3.04; Cl, 21.28; S, 38.73.

ILLUSTRATIVE PROCEDURE NO. 3

Preparation of 2-(4-chlorophenyl)ethanethiol

A mixture of 4-chlorophenethyl alcohol (50.0 g, 0.319 mole), thiourea (24.3 g, 0.319 mole) and 48% hydrobromic acid (161 g, 0.958 mole) was stirred under reflux for 9 hours. The mixture was cooled and a solution of sodium hydroxide (38.3 g, 0.958 mole) in water (380 ml) added, and the resulting mixture was stirred at reflux for 2 hours under a gentle stream of nitrogen. The mixture was cooled and the oily organic layer separated. The aqueous layer was acidified with hydrochloric acid and extracted with 3×50 ml portions of diethyl ether. The ethereal extracts were combined with the oily product and the combination washed with water followed by brine. The ethereal solution was dried (Na$_2$SO$_4$), concentrated and distilled to provide 34.5 g of the title compound, bp 72°–77° (0.03 mm).

EXAMPLE 1

1-[2,2-Bis(4-chlorobenzylthio)ethyl]-1H-imidazole Hydrochloride

A solution of 1-(2,2-diethoxyethyl)-1H-imidazole (3.68 g, 0.020 mole) and 4-chlorobenzyl mercaptan (6.35 g, 0.040 mole) in CHCl$_3$ (25 ml) was added dropwise during 90 minutes to a stirred, refluxing mixture of boron trifluoride etherate (4.8 ml, 0.038 mole) and acetic acid (10 ml) in CHCl$_3$ (15 ml). The mixture was then refluxed for 18 hours and concentrated to dryness. The residue was partitioned between diethyl ether and cold, dilute aqueous sodium hydroxide. The ethereal layer was washed with water, followed by brine and then dried over Na$_2$SO$_4$. Hydrogen chloride was bubbled into the ethereal filtrate to provide 6.5 g (82% yield) of the title compound mp 198°–200°. Recrystallization from ethanol afforded colorless crystals of the analytical sample, mp 196°–197.5°.

Anal. Calcd. for C$_{19}$H$_{18}$Cl$_2$N$_2$S$_2$.HCl: C, 51.18; H, 4.30; Cl, 23.85; N, 6.28; S, 14.38. Found: C, 50.97; H, 4.25; Cl, 23.27; N, 6.49; S, 14.18.

EXAMPLE 2

Repetition of the general procedure of Example 1, except that the 4-chlorobenzyl mercaptan utilized therein was replaced by (a) 4-chlorothiophenol,
(b) 4-methylthiophenol,
(c) 4-tert-butylthiophenol,
(d) benzyl mercaptan,
(e) 4-fluorobenzyl mercaptan,
(f) 2-chlorobenzyl mercaptan,
(g) 2,4-dichlorobenzyl mercaptan,
(h) 2,6-dichlorobenzyl mercaptan,
(i) 3-trifluoromethylbenzyl mercaptan,
(j) 4-methylbenzyl mercaptan,
(k) 4-methoxybenzyl mercaptan,
(l) 4-methylthiobenzyl mercaptan,
(m) 4-nitrobenzyl mercaptan,
(n) 2-(4-chlorophenyl)ethanethiol,
(o) 2-chloro-3-thienylmethyl mercaptan,
(p) 5-chloro-2-thienylmethyl mercaptan,
(q) n-octyl mercaptan and
(r) cyclohexylmethyl mercaptan, respectively, with the optional use of the indicated salt-forming acid, gave the following products, respectively:

(a) 1-[2,2-bis(4-chlorophenylthio)ethyl]-1H-imidazole, mp 122.5°–124.5°

Anal. Calcd. for C$_{17}$H$_{14}$Cl$_2$N$_2$S$_2$: C, 53.54; H, 3.70, Cl, 18.59; N, 7.35; S, 16.82. Found: C, 53.92; H, 3.83; Cl, 18.66; N, 7.39; S, 16.86.

(b) 1-[2,2-bis(4-methylphenylthio)ethyl]-1H-imidazole hydrochloride, mp 122°–124°

Anal. Calcd. for C$_{19}$H$_{20}$N$_2$S$_2$.HCl: C, 60.53; H, 5.62; N, 7.43; S, 17.01 Found: C, 60.55; H, 5.43; N, 7.64; S, 17.01.

(c) 1-[2,2-bis(4-tert-butylphenylthio)ethyl]-1H-imidazole hydrogen oxalate, mp 159.5°–160°

Anal. Calcd. for C$_{25}$H$_{32}$N$_2$S$_2$.C$_2$H$_2$O$_4$: C, 63.00; H, 6.66; N, 5.44; S, 12.46. Found: C, 62.74; H, 6.68; N, 5.22; S, 12.45.

(d) 1-[2,2-bis(benzylthio)ethyl]-1H-imidazole hydrochloride, mp 150°–151.5°

Anal. Calcd. for C$_{19}$H$_{20}$N$_2$S$_2$.HCl: C, 60.54; H, 5.61; Cl, 9.40; N, 7.43; S, 17.01. Found: C, 60.76; H, 5.65; Cl, 9.19; N, 7.78; S, 17.07.

(e) 1-[2,2-bis(4-fluorobenzylthio)ethyl]-1H-imidazole hydrochloride, mp 182°-184°

Anal. Calcd. for $C_{19}H_{18}F_2N_2S_2.HCl$: C, 55.26; H, 4.64; Cl, 8.59; N, 6.78. Found: C, 55.21; H, 4.61; Cl, 8.49; N, 6.96.

(f) 1-[2,2-bis(2-chlorobenzylthio)ethyl]-1H-imidazole hydrochloride, mp 175°-176°

Anal. Calcd. for $C_{19}H_{18}Cl_2N_2S_2.HCl$: C, 51.18; H, 4.30; Cl, 23.85; N, 6.28; S, 14.38. Found: C, 51.57; H, 4.29; Cl, 24.27, N, 6.54; S, 14.14.

(g) 1-[2,2-bis(2,4-dichlorobenzylthio)ethyl]-1H-imidazole, mp 104.5°-106°

Anal. Calcd. for $C_{19}H_{16}Cl_4N_2S_2$: C, 47.71; H, 3.37; Cl, 29.65; N, 5.86; S, 13.41. Found: C, 47.65; H, 3.43; Cl, 29.86; N, 5.91; S, 13.36.

The hydrochloride of the above compound had mp 174°-175°.

(h) 1-[2,2-bis(2,6-dichlorobenzylthio)ethyl]-1H-imidazole hydrogen oxalate, mp 179°-181°

Anal. Calcd. for $C_{19}H_{16}Cl_4N_2S_2.C_2H_2O_4$: C, 44.38; H, 3.19; N, 4.93; S, 11.28. Found: C, 44.58; H, 3.34; N, 5.20; S, 10.75.

(i) 1-[2,2-bis(3-trifluoromethylbenzylthio)ethyl]-1H-imidazole hydrochloride, mp 165.5°-167°

Anal. Calcd. for $C_{21}H_{18}F_6N_2S_2.HCl$: C, 49.17; H, 3.73; Cl, 6.91; N, 5.46. Found: C, 48.96; H, 3.60; Cl, 7.08; N, 5.61.

(j) 1-[2,2-bis(4-methylbenzylthio)ethyl]-1H-imidazole hydrochloride, mp 141°-143°

Anal. Calcd. for $C_{21}H_{24}N_2S_2.HCl$: C, 62.28; H, 6.22; Cl, 8.75; N, 6.92; S, 15.83. Found: C, 62.18; H, 6.30; Cl, 8.90; N, 6.99; S, 16.12.

(k) 1-[2,2-bis(4-methoxybenzylthio)ethyl]-1H-imidazole hydrochloride, mp 112°-113.5°

Anal. Calcd. for $C_{21}H_{24}N_2O_2S_2.HCl$: C, 57.72; H, 5.77; Cl, 8.11; N, 6.41; S, 14.67. Found: C, 57.92; H, 5.70; Cl, 8.09; N, 6.92; S, 14.84.

(l) 1-[2,2-bis(4-methylthiobenzylthio)ethyl]-1H-imidazole hydrochloride, mp 160°-161°

Anal. Calcd. for $C_{21}H_{24}N_2S_4.HCl$: C, 53.76; H, 5.37; Cl, 7.56; N, 5.97; S, 27.34. Found: C, 53.38; H, 5.26; Cl, 7.94; N, 6.28; S, 27.28.

(m) 1-[2,2-bis(4-nitrobenzylthio)ethyl]-1H-imidazole hydrochloride, mp 222°-224.5°

Anal. Calcd. for $C_{19}H_{18}N_4O_4S_2.HCl$: C, 48.87; H, 4.10; Cl, 7.59; N, 12.00; S, 13.73. Found: C, 48.95; H, 4.02; Cl, 7.54; N, 12.28; S, 13.60.

(n) 1-[2,2-bis(4-chlorophenethylthio)ethyl]-1H-imidazole hydrogen oxalate, mp 108°-109°

Anal. Calcd. for $C_{21}H_{22}Cl_2N_2S_2.C_2H_2O_4$: C, 52.37; H, 4.59; Cl, 13.44; N, 5.31; S, 12.16. Found: C, 52.44; H, 4.45; Cl, 12.96; N. 5.61; S, 12.14.

(o) 1-[2,2-bis(2-chloro-3-thienylmethylthio)ethyl]-1H-imidazole hydrochloride, mp 147°-149°

Anal. Calcd. for $C_{15}H_{14}Cl_2N_2S_4.HCl$: C, 39.35; H, 3.30; Cl, 23.23; N, 6.12; S, 28.01. Found: C, 39.31; H, 3.20; Cl, 23.01; N, 5.99; S, 27.83.

(p) 1-[2,2-bis(5-chloro-2-thienylmethylthio)ethyl]-1H-imidazole hydrochloride, mp 151°-152°

Anal. Calcd. for $C_{15}H_{14}Cl_2N_2S_4.HCl$: C, 39.35; H, 3.30; Cl, 23.23; N, 6.12; S, 28.01. Found: C, 39.38; H, 3.28; Cl, 23.12; N, 6.38; S, 28.66.

(q) 1-[2,2-bis(n-octylthio)ethyl]-1H-imidazole hydrochloride, mp 66°-69°

Anal. Calcd. for $C_{21}H_{40}N_2S_2.HCl$: C, 59.89; H, 9.81; Cl, 8.42; N, 6.65; S, 15.23. Found: C, 60.24; H, 10.24; Cl, 8.30; N, 6.56; S, 15.63.

(r) 1-[2,2-bis(cyclohexylmethylthio)ethyl]-1H-imidazole hydrochloride, mp 154°-156°

Anal. Calcd. for $C_{19}H_{32}N_2S_2.HCl$: C, 58.66; H, 8.55; Cl, 9.11; N, 7.20; S, 16.48. Found: C, 58.44; H, 8.44; Cl, 9.26; N, 7.44; S, 16.54.

EXAMPLE 3

1-[2,2-Bis(2,4-dichlorophenylthio)ethyl]-1H-imidazole Hydrochloride

A solution of 1-(2,2-diethoxyethyl)-1H-imidazole (1.84 g, 0.010 mole) and 2,4-dichlorothiophenol (3.56 g, 0.020 mole) in acetic acid (5 ml) was added dropwise during 5 minutes to a stirred, refluxing solution of boron trifluoride etherate (2.4 ml, 0.019 mole) in acetic acid (20 ml). The solution was refluxed for 24 hours and concentrated. The residue was partitioned between diethyl ether and dilute aqueous sodium hydroxide. The ethereal layer was washed with water, followed by brine and then dried over $Na_2SO_4$. Hydrogen chloride was bubbled into the ethereal filtrate to provide colorless crystals of the title compound (1.1 g), mp 156°-162°. Successive recrystallizations from ethanol-ether and chloroform-ether provided the analytical sample, mp 171°-171.5°.

Anal. Calcd. for $C_{17}H_{12}Cl_4N_2S_2.HCl$: C, 41.95; H, 2.69; Cl, 36.42; N, 5.76; S, 13.18. Found: C, 41.86; H, 2.70; Cl, 36.69; N, 5.75; S, 13.54.

EXAMPLE 4

1-[2-(4-Methylbenzylsulfinyl)-2-(4-methylbenzylthio)ethyl]-1H-imidazole Hydrochloride Diastereomer A and Diastereomer B A solution of 85% m-chloroperbenzoic acid (1.66 g, 9.63 mmoles) in chloroform (80 ml) was added dropwise during 1 hour to a stirred, cooled (ice/water) solution of 1-[2,2-bis(4-methylbenzylthio)ethyl]-1H-imidazole (3.55 g, 9.63 mmoles) in chloroform (125 ml). The solution was stirred for 18 hours at ambient temperature and then washed successively with aqueous $Na_2CO_3$ (2×), $H_2O$ and brine. The solution was dried over $Na_2SO_4$ and concentrated to leave a mixture of the diastereoisomeric mono-sulfoxides as a cloudy oil. Trituration of the oil with ether afforded the free base of diastereomer A (1.45 g), mp 86°-92° which was converted into the hydrochloride salt, mp 167°-170° with ethereal hydrogen chloride. Hydrogen chloride was bubbled into the ethereal mother liquor from the trituration step to give a mixture of the hydrochloride salts which after recrystallization from acetonitrile provided additional diastereomer A, mp 164°-168° (0.42 g) and 0.57 g of diastereomer B, mp 141°-146°.

The two fractions with respective melting points of 164°-168° and 167°-170° were combined and recrystallized from acetonitrile to provide colorless crystals of diastereomer A, mp 178°-180°. Diastereomer B was recrystallized from acetonitrile-ether to afford colorless crystals, mp 152°-155°.

Anal. Calcd. for $C_{21}H_{24}N_2OS_2.HCl$: C, 59.91; H, 5.99; Cl, 8.42; N, 6.65; S, 15.23. Found (diastereomer A): C, 59.83; H, 5.98; Cl, 8.28; N, 6.83; S, 15.08. Found (diastereomer B): C, 59.81; H, 5.97; Cl, 8.33; N, 6.80; S, 15.51.

EXAMPLE 5

1-[2-(4-Chlorobenzylthio)-2-(4-chlorophenylthio)ethyl]-1H-imidazole Hydrochloride A solution of 1-(2,2-diethoxyethyl)-1H-imidazole (3.68 g, 0.020 mole), 4-chlorothiophenol (2.88 g, 0.020 mole) and 4-chlorobenzyl mercaptan (3.16 g, 0.020 mole) in chloroform (50 ml) was added dropwise during 30 minutes to a stirred, refluxing mixture of boron trifluoride etherate (4.8 ml, 0.036 mole) and acetic acid (10 ml) in chloroform (30 ml). The mixture was stirred under reflux for 18 hours and concentrated. The residue was partitioned between diethyl ether and cold aqueous sodium hydroxide. The organic layer was washed with water (2×) followed by brine and dried over $Na_2SO_4$. Hydrogen chloride was bubbled into the ethereal filtrate to afford a mixture of the hydrochloride salts of the three possible mercaptals. The mixture was crystallized from ethanol-ether to yield 1.4 g of 1-[2,2-bis(4-chlorobenzylthio)ethyl]-1H-imidazole hydrochloride, mp 180°–183°. Dilution of the mother liquor with additional ether provided 2.2 g of the title compound, mp 135°–137°, which melted at 136°–139° after recrystallization from chloroform-ether.

Anal. Calcd. for $C_{18}H_{16}Cl_2N_2S_2 \cdot HCl$: C, 50.07; H, 3.97; Cl, 24.63; N, 6.49; S, 14.85. Found: C, 50.28; H, 3.98; Cl, 24.54; N, 6.66; S, 14.57.

The results of gas-liquid chromatography from a similar experiment showed the crude mixture of free bases to consist of: 3% of 1-[2,2-bis(4-chlorophenylthio)ethyl]-1H-imidazole, 55% of the title compound and 22% of 1-[2,2-bis(4-chlorobenzylthio)ethyl]-1H-imidazole.

EXAMPLE 6

1-[2-(4-Chlorophenylthio)-2-(4-methylbenzylthio)ethyl]-1H-imidazole Hydrogen Oxalate A solution of 1-(2,2-diethoxyethyl)-1H-imidazole (2.43 g, 0.0132 mole), 4-methylbenzyl mercaptan (1.83 g, 0.0132 mole) and 4-chlorothiophenol (1.91 g, 0.0132 mole) in chloroform (25 ml) was added dropwise during 20 minutes to a stirred, slowly refluxing solution of boron trifluoride etherate (3.17 ml, 0.0238 mole) and acetic acid (7 ml) in chloroform (20 ml). The mixture was refluxed for 20 hours and concentrated. The residue was partitioned between diethyl ether and aqueous sodium hydroxide. The ethereal layer was washed with water followed by brine and dried over $Na_2SO_4$. Removal of the ether left a viscous oil (4.1 g) which was shown by gas-liquid chromatography to be a mixture of free bases consisting of the title compound (56%) and 1-[2,2-bis(4-methylbenzylthio)ethyl]-1H-imidazole (28%).

A solution of the mixture (4.1 g) in ethyl acetate, when treated with oxalic acid (0.9 g), deposited two crops of colorless crystals: crop A (2.9 g) mp 107°–110° and crop B (1 g), mp 131°–133°. Crop B was successively recrystallized from acetonitrile and then ethanol to provide a mixture of the title compound, mp 138°–138.5° containing about 15% of 1-[2,2-bis(4-methylbenzylthio)ethyl]-1H-imidazole.

EXAMPLE 7

1-[2,2-Bis(4-cyanobenzylthio)ethyl]-1H-imidazole Hydrochloride

A solution of 1-(2,2-diethoxyethyl)-1H-imidazole (6.0 g, 0.0326 mole) and 4-cyanobenzyl mercaptan (9.72 g, 0.0651 mole) in $CHCl_3$ (50 ml) was added dropwise during 15 minutes to a stirred, refluxing mixture of boron trifluoride etherate (7.62 ml, 0.062 mole) and acetic acid (17 ml) in $CHCl_3$ (50 ml). The mixture was stirred under reflux for 20 hours and concentrated to dryness. The residue was partitioned between $CH_2Cl_2$ and cold 15% aqueous sodium hydroxide, and the aqueous layer was re-extracted with $CH_2Cl_2$. The combined $CH_2Cl_2$ layers were washed successively with dilute sodium hydroxide, water and brine, and then dried over $Na_2SO_4$. The $CH_2Cl_2$ was removed and a solution of the residue in ethanol-ether was treated with hydrogen chloride to provide colorless crystals (7.5 g) of the title compound, mp 209°–213°. Two recrystallizations from ethanol afforded the analytical sample, mp 216.5°–217.5°.

Anal. Calcd. for $C_{21}H_{18}N_4S_2 \cdot HCl$: C, 59.07; H, 4.49; Cl, 8.30; N, 13.12; S, 15.02 Found: C, 58.67; H, 4.60; Cl, 8.48; N, 13.23; S, 14.81.

EXAMPLE 8

1-[2,2-Bis(4-carbomethoxybenzylthio)ethyl]-1H-imidazole Hydrochloride

1-[2,2-Bis(4-cyanobenzylthio)ethyl]-1H-imidazole hydrochloride (1.43 g) was added to methanol (50 ml) which had been saturated with hydrogen chloride at 0°. The resulting solution was stirred under reflux for 20 hours and concentrated. The gummy residue was partitioned between $CH_2Cl_2$ and aqueous $NaHCO_3$, and the $CH_2Cl_2$ layer was washed with brine and dried over $Na_2SO_4$. Removal of the $CH_2Cl_2$ left a gum which was chromatographed on silicic acid (60 g) with $CH_2Cl_2/CH_3OH$ (95:5), to afford 1.1 g of the free base of the title compound as a viscous oil. Treatment of a solution of the base in $CH_3OH$-ether with hydrogen chloride provided colorless crystals of the title compound, mp 176.5°–178°. Recrystallization from $CH_3OH$-ether afforded the analytical sample, mp 178°–179°.

Anal. Calcd. for $C_{23}H_{24}N_2S_2O_4 \cdot HCl$: C, 56.03; H, 5.11; Cl, 7.19; N, 5.68; S, 13.01. Found: C, 56.13; H, 5.09; Cl, 7.25; N, 5.83; S, 13.18.

EXAMPLE 9

1-[2,2-Bis(4-aminobenzylthio)ethyl]-1H-imidazole Trihydrochloride

A stirred mixture of 1-[2,2-bis(4-nitrobenzylthio)ethyl]-1H-imidazole (924 mg), iron powder (1.08 g) and ammonium chloride (862 mg) in water (30 ml) was refluxed for 2 hours. The cooled mixture was thoroughly extracted with $CH_2Cl_2$ and the combined $CH_2Cl_2$ extracts were washed with water and dried over $Na_2SO_4$. Removal of the $CH_2Cl_2$ left 360 mgs. of the crude amine as a viscous oil. The black residue, which resisted extraction with $CH_2Cl_2$, was extracted with dilute aqueous oxalic acid. The aqueous mixture was filtered, and the filtrate was made basic with aqueous potassium hydroxide. Extraction of the filtrate with $CH_2Cl_2$ gave another crop of the crude amine which was combined with the 360 mg. fraction. The crude amine was chromatographed on silicic acid (20 g) with $CH_2Cl_2/CH_3OH$/diethyl amine (500:25:2) to afford 340 mg. of the pure amine. Treatment of a solution of the pure base in ethanol with hydrogen chloride afforded the title compound as a light tan amorphous solid which melted indistinctly with decomposition.

Anal. Calcd. for $C_{19}H_{22}N_4S_2 \cdot 3HCl$: C, 47.55; H, 5.25; Cl, 22.16; N, 11,67; S, 13.36. Found: C, 47.16; H, 5.43; Cl, 21.60; N, 11.23; S, 13.37.

EXAMPLE 10

1-[2,2-Bis(α-methylbenzylthio)ethyl]-1H-imidazole Hydrochloride

A solution of 1-(2,2-diethoxyethyl)-1H-imidazole (3.68 g, 0.02 mole) and α-methylbenzyl mercaptan (5.53 g, 0.04 mole) in $CHCl_3$ (25 ml) was added dropwise during 20 minutes to a stirred, refluxing mixture of boron trifluoride etherate (4.8 ml, 0.038 mole) and acetic acid (10 ml) in $CHCl_3$ (15 ml). The mixture was stirred under reflux for 18 hours and concentrated to dryness. The residue was partitioned between ether and 10% aqueous sodium hydroxide. The ethereal layer was washed with three portions of $H_2O$, followed by brine, and then dried over $Na_2SO_4$. The ether was removed and the residue chromatographed on silicic acid (200 g) with $CH_2Cl_2/CH_3OH$ (100:4) to provide 5.69 g of the free base of the title compound which is a mixture of all the possible stereoisomers (one dl-pair which can be resolved into enantiomers and two meso forms), as shown by a 100 MHz NMR spectrum.

A solution of the mixed stereoisomeric base in ether was treated with hydrogen chloride to provide the hydrochloride salt, mp 141°–165°. Recrystallization from acetonitrile afforded two crops of colorless crystals: 2 g, with mp 182°–189° and 0.9 g with mp 169°–184°. The acetonitrile mother liquor was concentrated to dryness and the residue was digested with boiling ethyl acetate to provide a third crop of material with mp 150°–158° (0.4 g). Successive recrystallizations from acetonitrile and ethanol of the material with mp 182°–189° gave one substantially pure meso form or dl-pair of the title compound with mp 188°–189°, as shown by a 100 MHz NMR spectrum. The material with mp 150°–158° was recrystallized from ethanol-ether to afford colorless crystals of the title compound, mp 147°–156°, which was shown by a 100 MHz NMR spectrum to be approximately a 1:1:1 mixture of the two meso forms and the dl-pair.

Anal. Calcd. for $C_{21}H_{24}N_2S_2 \cdot HCl$: C, 62.28; H, 6.22; Cl, 8.75; N, 6.92; S, 15.83. Found (mp 188°–189°): C, 62.04; H, 6.18; Cl, 9.01; N, 7.07; S, 15.72. Found (mp 147°–156°): C, 61.86; H, 6.23; Cl, 8.36; N, 7.04; S, 15.71.

EXAMPLE 11

1-[2-(4-Chlorophenylthio)-2-(2,6-dichlorobenzylthio)ethyl]-1H-imidazole Hydrochloride A solution of 4-chlorothiophenol (2.13 g, 0.015 mole), 2,6-dichlorobenzyl mercaptan (2.90 g, 0.015 mole) and 1-(2,2-diethoxyethyl)-1H-imidazole (5.52 g, 0.03 mole) in $CHCl_3$ (90 ml) was added to a stirred solution of boron trifluoride etherate (12 ml, 0.095 mole) and acetic acid (30 ml) in $CHCl_3$ (60 ml). The mixture was stirred under reflux for 24 hours and concentrated. The residue was partitioned between $CH_2Cl_2$ and dilute aqueous sodium hydroxide, and the $CH_2Cl_2$ layer was dried over $MgSO_4$ and concentrated to leave 5.6 g of a gum. High performance liquid chromatography (HPLC) employing an analytical μ-porasil column and a mixture of toluene/isooctane/2-propanol/ammonium hydroxide (100:100:2:1) as the mobile phase showed the gum to be a mixture of bases containing the title compound, 1-[2,2-bis(4-chlorophenythio)ethyl]-1H-imidazole and 1-[2,2-bis(2,6-dichlorobenzylthio)ethyl]-1H-imidazole. A solution of the bases in acetone, when treated with 1.1 ml of concentrated hydrochloric acid, deposited 4.7 g of a mixture of hydrochloride salts. Two recrystallizations from 95% ethanol provided 1.32 g of substantially pure title compound (as shown by HPLC) with mp 195°–201°.

Anal. Calcd. for $C_{18}H_{15}Cl_3N_2S_2 \cdot HCl$: C, 46.36; H, 3.46; Cl, 30.42; N, 6.01; S, 13.75. Found: C, 46.54; H, 3.39; Cl, 30.84; N, 6.22; S, 13.84.

EXAMPLE 12

1-[2,2-Bis(3-chloro-4-methylbenzylthio)ethyl]-1H imidazole

A solution of 1-(2,2-diethoxyethyl)-1H-imidazole (3.32 g, 0.0180 mole) and 3-chloro-4-methylbenzyl mercaptan (6.23 g, 0.0361 mole) in chloroform (35 ml) was added dropwise, over a period of 20 minutes, to a stirred, refluxing solution of boron trifluoride etherate (4.1 ml, 0.0325 mole) and acetic acid (10 ml) in chloroform (27 ml). The solution was refluxed for 20 hours and concentrated to dryness. The residue was partitioned between ether and dilute aqueous sodium hydroxide. The ethereal layer was washed with water and brine, and dried over $Na_2SO_4$. Hydrogen chloride was bubbled into the ethereal solution to give 7.6 g of product as the HCl salt, mp 174°–177°. The product was recrystallized from ethanol-ether to give colorless crystals of the title compound as its HCl salt, mp 183°–184°.

Anal. Calcd. for $C_{21}H_{22}Cl_2N_2S_2 \cdot HCl$: C, 53.22; H, 4.89; N, 5.91; Cl, 22.44; S, 13.53 Found: C, 53.29; H, 4.93; N, 6.16; Cl, 22.27; S, 13.82.

EXAMPLE 13

The general procedure of Example 1 is repeated except that the 4-chlorobenzyl mercaptan utilized therein is replaced by an equimolar amount of
2-thienyl mercaptan,
4-vinylbenzyl mercaptan,
2-mercaptobenzoic acid,
n-butyl mercaptan,
thiophenol,
2-mercaptopyridine,
cyclohexyl mercaptan,
2-pyridylmethyl mercaptan and
4-(dimethylamino)benzyl mercaptan, respectively,
and there is thereby produced
1-[2,2-bis(2-thienylthio)ethyl]-1H-imidazole,
1-[2,2-bis(4-vinylbenzylthio)ethyl]-1H-imidazole,
1-[2,2-bis(n-butylthio)ethyl]-1H-imidazole,
1-[2,2-bis(phenylthio)ethyl]-1H-imidazole,
1-[2,2-bis(2-pyridylthio)ethyl]-1H-imidazole,
1-[2,2-bis(cyclohexylthio)ethyl]-1H-imidazole,
1-[2,2-bis(2-pyridylmethylthio)ethyl]-1H-imidazole and
1-[2,2-bis(4-dimethylaminobenzylthio)ethyl]-1H-imidazole,
respectively. Treatment of the free bases of these compounds in ethanol solution with hydrogen chloride produces the respective hydrochloride salts.

Example 14

1-[2,2-Bis(4-acetylaminobenzylthio)ethyl]-1H-imidazole Hydrochloride

A solution of 1-[2,2-bis(4-aminobenzylthio)ethyl]-1H-imidazole (prepared in Example 9) and a small excess of acetic anhydride in methylene chloride is refluxed for 30 minutes. The reaction mixture is worked up to give the free base of the title compound, which is dissolved in ethanol and treated with hydrogen chloride to give the hydrochloride salt.

EXAMPLE 15

1-[2,2-Bis(4-ethylaminobenzylthio)ethyl]-1H-imidazole Trihydrochloride

1-[2,2-Bis(4-acetylaminobenzylthio)ethyl]-1H-imidazole (prepared in Example 15) is dissolved in tetrahydrofuran and treated with a small excess of lithium aluminum hydride at reflux temperature for 45 minutes. The excess reducing agent is decomposed and the reaction mixture is worked up to give the free base of the title compound. The free base is dissolved in ethanol and treated with hydrogen chloride to give the trihydrochloride salt.

We claim:

1. The compound which is 1-[2,2-bis(4-methoxybenzylthio)ethyl]-1H-imidazole, or a pharmaceutically acceptable acid addition salt thereof.

2. The compound which is 1-[2,2-bis(4-methylthiobenzylthio)ethyl]-1H-imidazole, or a pharmaceutically acceptable acid addition salt thereof.

3. The compound which is 1-[2,2-bis(4-nitrobenzylthio)ethyl]-1H-imidazole, or a pharmaceutically acceptable acid addition salt thereof.

4. The compound which is 1-[2,2-bis(4-chlorophenethylthio)ethyl]-1H-imidazole, or a pharmaceutically acceptable acid addition salt thereof.

5. The compound which is 1-[2,2-bis(cyclohexylmethylthio)ethyl]-1H-imidazole, or a pharmaceutically acceptable acid addition salt thereof.

6. The compound which is 1-[2-(4-methylbenzylsulfinyl)-2-(4-methylbenzylthio)ethyl]-1H-imidazole, or a pharmaceutically acceptable acid addition salt thereof.

7. The compound which is 1-[2,2-bis(4-carbomethoxybenzylthio)ethyl]-1H-imidazole, or a pharmaceutically acceptable acid addition salt thereof.

8. The compound which is 1-[2,2-bis(4-cyanobenzylthio)ethyl]-1H-imidazole, or a pharmaceutically acceptable acid addition salt thereof.

9. The compound which is 1-[2,2-bis(4-aminobenzylthio)ethyl]-1H-imidazole, or a pharmaceutically acceptable acid addition salt thereof.

* * * * *